United States Patent [19]

Cain

[11] 4,321,829
[45] Mar. 30, 1982

[54] DENSITY MEASURING APPARATUS

[75] Inventor: David E. Cain, Houston, Tex.

[73] Assignee: Halliburton Company, Duncan, Okla.

[21] Appl. No.: 130,964

[22] Filed: Mar. 17, 1980

[51] Int. Cl.³ .............................................. G01N 9/02
[52] U.S. Cl. ..................................................... 73/433
[58] Field of Search .............................. 73/433–437; 177/246, DIG. 9, 149

[56] References Cited

U.S. PATENT DOCUMENTS

| 460,147 | 9/1891 | Parish | 177/DIG. 9 |
|---|---|---|---|
| 1,671,127 | 5/1928 | Reufel | 177/246 |
| 2,132,736 | 10/1938 | Jones | 73/433 |
| 3,057,421 | 10/1962 | Fann | 177/246 |
| 3,354,971 | 11/1967 | Vash et al. | 177/246 |
| 3,747,415 | 7/1973 | Nickles et al. | 73/433 |
| 4,050,531 | 9/1977 | Ashbrook | 177/246 |

FOREIGN PATENT DOCUMENTS

| 1006622 | 4/1957 | Fed. Rep. of Germany | 73/433 |
|---|---|---|---|
| 73134 | 4/1953 | Netherlands | 177/246 |

Primary Examiner—James J. Gill
Attorney, Agent, or Firm—Thomas R. Weaver; John H. Tregoning; Lucian Wayne Beavers

[57] ABSTRACT

A density measuring apparatus includes a container for holding a fluid to be tested, a balance arm having a first end attached to the container, a fulcrum for supporting the balance arm, and a balance weight slidably disposed on the balance arm. The balance arm has an inverted channel shape cross-section defined by a top portion and first and second side portions depending downwardly from the top portion. First and second tabs extend downwardly from the first and second side portions and have first and second downward opening recesses disposed therein, respectively. A knife edge of the fulcrum engages the recesses of the tabs so that the balance arm is supported thereby. Approximately one-third of the length of the balance arm adjacent the container includes a longitudinally extending rib member located intermediate of the first and second side portions and depending downward from the top portion of the balance arm. A tab of the rib member extends downward therefrom and engages a notch in the knife edge of the fulcrum.

3 Claims, 10 Drawing Figures

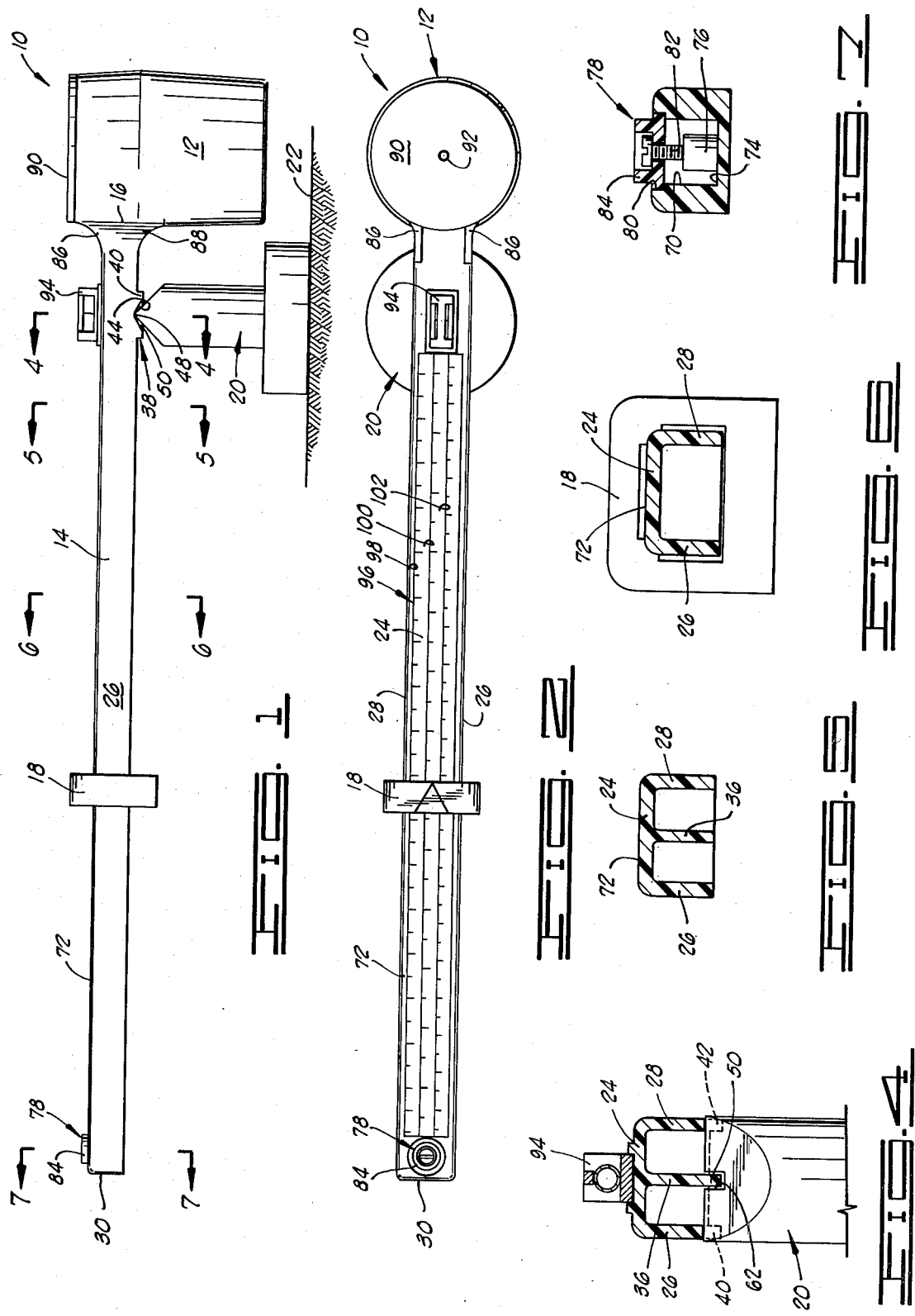

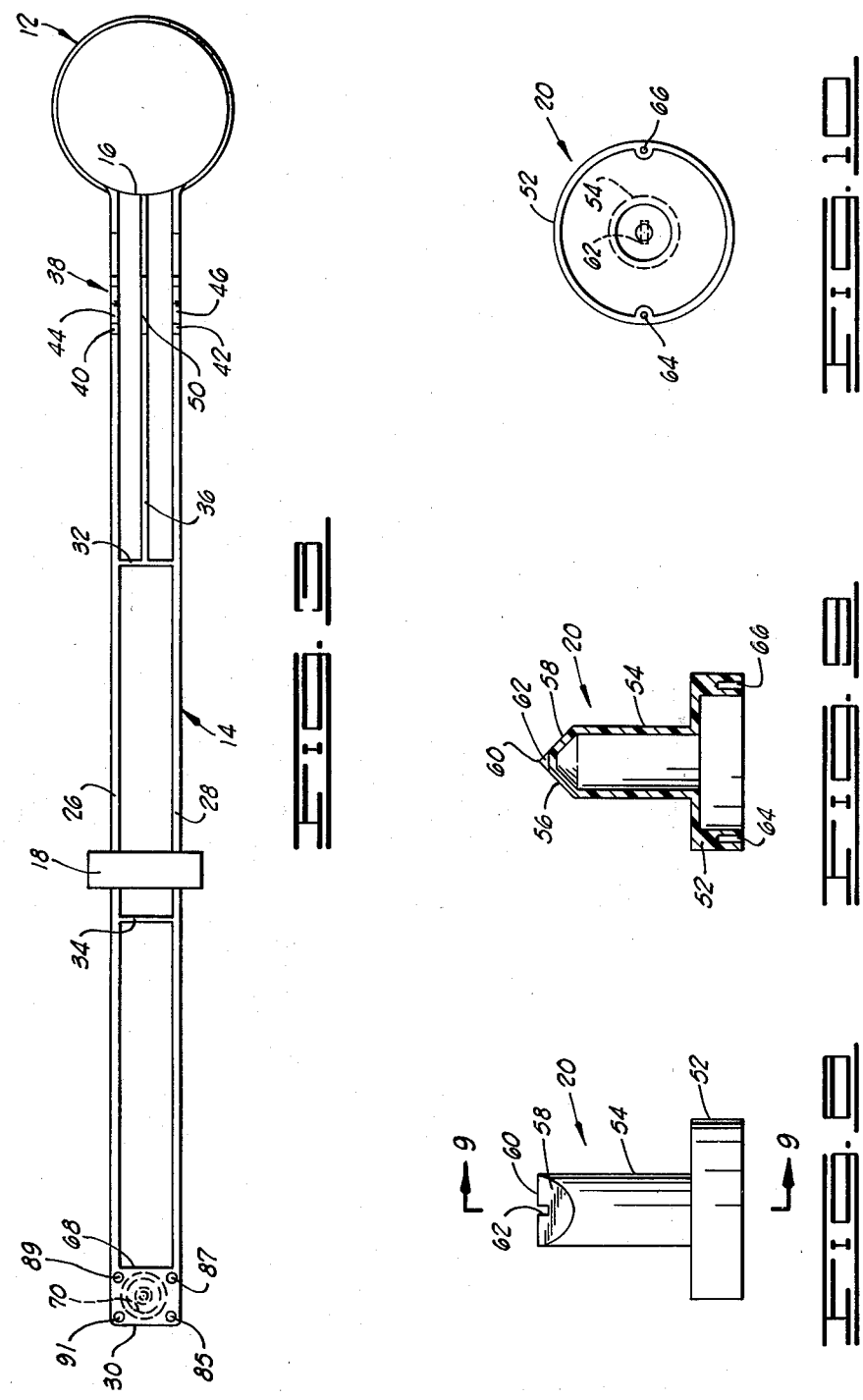

DENSITY MEASURING APPARATUS

The following invention relates generally to apparatus for measuring the density of a fluid, and more particularly, but not by way of limitation, to an apparatus for measuring the density of a sample of drilling mud.

In the drilling of oil wells, drilling fluid, called mud, is used to cool and lubricate the drilling bit and to remove rock fragments cut by the bit. It is very important during the drilling process to be able to rapidly and accurately determine the density of the mud being pumped into the well.

Another fluid utilized in the drilling of wells is cement. The present invention may be also used to measure the density of this cement.

Various devices are used in determining the densities in the oil fields, with the most common device being referred to as a mud balance. A mud balance typically includes a fluid container, a balance arm extending from the container, a fulcrum for supporting the balance arm, and a balance weight slidably disposed on the balance arm. The container which has a constant volume is located on one side of the fulcrum support, and the sliding balance weight is located on the other side of the fulcrum support. In operation, the container is filled with mud, and the density of the mud is determined by sliding the balance weight until the balance arm is balanced on the fulcrum support means. Scale indicia are provided on the balance arm for indicating the density corresponding to a given position of the balance weight in the balanced condition.

The general operating procedure and industry standards for mud balances are found in American Petroleum Institute Bulletin "RP 13B: Standard Procedure for Testing Drilling Fluids", (7th Ed., April, 1978). Typical testing procedures are described at page 3 of that Bulletin. Two examples of prior art mud balances are shown at page 4 of that Bulletin in FIGS. 1.1 and 1.2. The mud balance shown in FIG. 1.1 of the Bulletin is a type manufactured by the Baroid Division of National Lead Co., Houston, Tex. The apparatus shown at FIG. 1.2 of the Bulletin is a type manufactured by the Fann Instrument Co., Houston, Tex.

Another mud balance is illustrated in U.S. Pat. No. 3,747,415 to Nickles, et al., and assigned to the assignee of the present invention. Another such device manufactured by the Halliburton Company, the assignee of the present invention, is one designated by the trademark "Halliburton Tru-Wate Cup" and illustrated in brochure "SP-11053" dated June, 1972.

To appreciate the improvements provided by the density measuring apparatus of the present invention, it is desirable to have an understanding of the field environment in which the apparatus is used. The apparatus is generally used at an oil well drilling site. The apparatus must be carried around from site to site by the persons doing the testing of the drilling mud, and it is subjected to severe environmental conditions in terms of rough handling and the corrosive nature of the materials with which it comes in contact.

It is, therefore, desirable to provide a very rugged, yet lightweight density measuring apparatus which is so constructed that it can be easily handled, can withstand rough treatment, and is relatively unaffected by a wet, dirty, corrosive environment.

The density measuring apparatus of the present invention is of such a design that it may be manufactured from relatively lightweight corrosion resistant thermoplastic materials, as contrasted to the heavier metallic materials generally used by the prior art, while still providing a rugged and structurally durable instrument.

The density measuring apparatus of the present invention includes a container for holding the mud to be tested, a balance arm having a first end attached to the container, a fulcrum means for supporting the balance arm, and a balance weight slidably disposed on the balance arm. The balance arm is characterized in that it has an inverted channel shape cross-section defined by a top portion and first and second side portions depending downwardly from said top portion. A support means is provided on the balance arm and is comprised of first and second tabs extending downwardly from the first and second side portions, and having first and second downward opening recesses disposed therein. A knife edge of the fulcrum means engages the recesses of the tabs so that the balance arm is supported thereby. Approximately one-third of the length of the balance arm adjacent the container means also has a longitudinally extending rib member located intermediate of of the first and second side portions and depending downward from the top portion of the balance arm. This rib member provides additional structural support at the point on the balance arm supported by the fulcrum, so that additional strength is provided at the most highly stressed portion of the balance arm.

A tab of this rib member extends downward therefrom and engages a notch in the knife edge of the fulcrum so as to prevent the balance arm from sliding sideways off the knife edge.

This construction generally provides a structurally sound yet lightweight and corrosion resistant mud balance.

Numerous objects, features and advantages of the present invention will be readily apparent to those skilled in the art upon a reading of the following disclosure when taken in conjunction with the accompanying drawings.

FIG. 1 is a side elevation view of the density measuring apparatus of the present invention.

FIG. 2 is a plan view of the apparatus of FIG. 1.

FIG. 3 is a bottom view of the balance arm and container.

FIG. 4 is a sectional elevation view about line 4—4 of FIG. 1 illustrating the details of construction of the support means of the balance arm.

FIG. 5 is a sectional elevation view about line 5—5 of FIG. 1, illustrating the typical cross section of that portion of the balance arm containing the intermediate rib member.

FIG. 6 is a sectional elevation view about line 6—6 of FIG. 1.

FIG. 7 is a sectional elevation view about line 7—7 of FIG. 1, illustrating the construction of the calibration well at the second end of the balance arm.

FIG. 8 is an elevation view of the fulcrum means.

FIG. 9 is a sectional elevation view taken about line 9—9 of FIG. 8.

FIG. 10 is a bottom view of the fulcrum of FIG. 8.

Referring now to the drawings, and particularly to FIG. 1, the density measuring apparatus of the present invention is shown and generally designated by the numeral 10. The apparatus 10 includes a container means 12, for receiving and holding the fluid the density of which is being measured. A balance arm 14 has a first end 16 attached to container 12. A stainless steel balance weight 18 is slidably disposed on balance arm 14.

A fulcrum means generally designated by the numeral 20 supports the apparatus 10 from a ground surface 22. The ground surface 22, of course, may be a flat planar surface such as a table top.

As is best seen in FIGS. 4, 5 and 6, the balance arm 14 has an inverted channel shape cross-section defined by a top portion 24 and first and second side portions 26 and 28, depending downwardly from top portion 24. A width of top portion 24 is greater than a height of side portions 26 and 28. In a preferred embodiment, the width of top member 24 is 0.950 inches and the height of first and second side portions 26 and 28 is 0.625 inches. The thickness of top portion 24 and first and second side portions 26 and 28 is approximately 0.10 inches.

The length of balance arm 14 between first end 16 and a second end 30 thereof, is divided into three sections by first and second reinforcing webs 32 and 34, respectively, which span between top portion 24 and first and second side portions 26 and 28. Each of these three portions comprises approximately one-third the length of balance arm 14.

The portion of balance arm 14 between first end 16 and first reinforcing web 32 includes an intermediate rib member 36 extending downward from top portion 24 and extending longitudinally from first end 16, where it is attached to container 12, to the first reinforcing web 32 which is connected to rib 36. Rib 36 is parallel to first and second side portions 26 and 28 of balance arm 14.

The provision of the intermediate rib 36 along only the approximately one-third of balance arm 14 nearest to container 12 is in fact preferable to providing rib 36 along the entire length of balance arm 14 for the following reasons. The additional weight of extending rib 36 the entire length of balance arm 14 would require the weight of the container means 12 to be increased or would require the container means 12 to be moved further away from fulcrum means 20, neither of which is desirable. Alternatively, the container means 12 could be made larger, but that is also undesirable because more fluid would be required to make a test. Additionally, extending the rib 36 would require more material for the construction of the balance arm 14.

Balance arm 14 includes a support means, generally designated by the numeral 38, for engaging fulcrum means 20 so that balance arm 14 is supported by fulcrum 20 at a point of engagement therebetween.

Support means 38 includes first and second tabs 40 and 42, extending downward from first and second side portions 26 and 28, respectively. Tabs 40 and 42 have first and second downward opening recesses 44 and 46 disposed therein, respectively, for receiving fulcrum means 20. The recesses 44 and 46 are inverted V-shaped notches having a radiused root for engaging fulcrum means 20. The root 48 of notch recess 44 is preferably radiused 1/16 inch.

Rib member 36 includes a third downward extending tab 50 which is generally rectangular shaped portion extending downward from rib 36 at a location between tabs 40 and 42.

The support means 20 includes a disk shaped base 52 having a cylindrical leg 54 extending upward therefrom. The upper end of leg 54 has first and second oppositely sloped surfaces 56 and 58 which define a knife edge 60 at their peak. It is the knife edge 60 which engages recesses 44 and 46 of tabs 40 and 42 of support means 38.

The knife edge 60 has an upward opening recess 62 disposed therein for receiving tab 50 of third rib 36 when knife edge 60 is engaged with balance arm 14.

As is best seen in FIG. 9, the base 52 and leg 54 of fulcrum means 20 are hollow members. The base 52 includes first and second screw receiving holes 64 and 66 for attaching fulcrum means 20 to the bottom of a carrying case (not shown) in which the apparatus 10 is generally carried and mounted.

The tabs 40 and 42 are provided on balance arm 14 so that support means 38 can be formed without substantially decreasing the cross-sectional area of the inverted channel shaped balance arm 14. The stresses on balance arm 14 are the greatest at the point of engagement with fulcrum means 20 when in use, and near container 12 when the container 12 is turned upside down and rapped on a solid surface to remove the mud sample therefrom. Therefore it is important that the strength of balance arm 14 not be decreased at that point of engagement. The area of the inverted channel shape cross-section (top 24 and sides 26 and 28) taken through recesses 44 and 46 of tabs 40 and 42 of support means 38 is substantially as great as an area of said inverted channel shape crosssection closely adjacent said tabs which would appear the same as that shown in FIG. 5.

The strength of balance arm 14 at support means 38 is also increased by the presence of rib member 36, which provides approximately a 30% greater moment of inertia in the cross-section shown in FIG. 5 as compared to the cross-section shown in FIG. 6.

The inverted channel shape cross-section of balance arm 14 is terminated a short distance from second end 30 of balance arm 14 at an end wall 68, as shown in FIG. 3. Between wall 68 and second end 30 of balance arm 14 there is disposed a calibration well 70 in the top surface 72 of balance arm 14. The calibration well 70 is a generally cylindrical shaped opening. Extending upwardly from a bottom surface 74 of calibration well 70 is a screw receiving post 76.

A calibration well cover means 78 is placed in a shallow counter bore 80 of calibration well 70 after a plurality of B—B shot (not shown) or other calibration weight means have been placed therein. A screw 82 is disposed through cover means 78 and attaches the same to screw receiving post 76. Cover means 78 includes an upwardly extending portion 84 which provides a means for preventing balance weight 18 from sliding off second end 30 of balance arm 14.

As is best seen in FIG. 3, four cylindrical holes 85, 87, 89, and 91 are disposed in the bottom surface of balance arm 14, around the calibration well 70. These holes reduce the amount of material required for construction of balance arm 14, and also reduce the wall thickness of the molded part near calibration well 70.

At the connection between first end 16 of balance arm 14 and container means 12, a portion of radiused gusset material such as shown at 86 and 88 reinforces the connection between first and second side portions 26 and 28 and the container means 12.

A cover 90 is provided on container 12 and has a relief hole 92 disposed therein.

Attached to top member 24 of balance arm 14 at a location directly above fulcrum means 20 is a bubble type level indicator 94.

Located on top surface 72 of top portion 24 of balance arm 14 is a longitudinally displayed indicia means 96 which is operably associated with balance weight 18 so that a portion of indicia means 96 corresponding to a given position of balance weight 18 indicates a density of the mud contained in the container 12 when the balance arm 14 is balanced on fulcrum means 20.

The indicia means 96 includes first, second and third parallel indicia scales 98, 100 and 102. The three indicia scales preferably provide density information in units of $Kg/m^3$, $lb/ft^3$, and lb/gal.

One advantage of placing all three indicia means 98, 100 and 102 on the top surface 72 is that they may all be viewed from a single location. Several of the prior art devices described above, distribute the various scales used therewith on opposite sides of the balance arm so that they cannot all be viewed from a single location, and in fact making scales on the back sides of the balance arm impossible to view when the apparatus is disposed in a carrying case.

The balance arm 14, container 12 and fulcrum means 20 are all preferably constructed from a thermoplastic material. The balance arm 14 and container 12 comprise a single integrally molded thermoplastic part. Any thermoplastic material utilized for the apparatus 10 must have a satisfactory operation temperature range, high strength, durability, and chemical resistance. Thermoplastic materials which can be constructed to have the proper properties include glass-filled polyester, glass-filled nylon, glass-filled acetel, glass-filled polypropylene, and ABS. The balance arm 14 and container means 12 preferably comprise a single integrally molded thermoplastic part. The fulcrum means 20 preferably comprises a second integrally molded thermoplastic part.

The indicia means 96 is preferably etched into top surface 72 of thermoplastic balance arm 14.

This, it is seen that the density measuring apparatus of the present invention provides an improved, lightweight rugged and corrosion resistant density measuring apparatus which attains the ends and advantages mentioned as well as those inherent therein. While presently preferred embodiments of the invention have been described for the purpose of this disclosure, numerous changes in the arrangement and construction of parts may be made by those skilled in the art and are included within the scope and spirit of the present invention as defined by the appended claims.

What is claimed is:

1. An apparatus for measuring density of a fluid, comprising:
   a container means for holding said fluid;
   a balance arm having a first end attached to said container means, said arm having an inverted channel shaped crosssection defined by a top portion and first and second side portions depending downwardly from said top portion, and said arm including a rib member extending downward from said top portion between said first and second side portions, said rib member extending along at least a portion of a length of said balance arm;
   a fulcrum means for supporting said balance arm;
   a balance weight, slidably disposed on said balance arm;
   wherein said balance arm includes a support means for engaging said fulcrum means, so that said balance arm is supported by said fulcrum means, said support means including first and second tabs extending downward from said first and second side portions, respectively, said first and second tabs having first and second downward opening recesses disposed therein, respectively, for receiving said fulcrum means; and
   wherein said fulcrum means includes a knife edge means for engaging said support means of said balance arm, said knife edge means having an upward opening recess disposed therein in which said rib member of said balance arm is received when said knife edge means is engaged with said support means of said balance arm.

2. An apparatus for measuring density of a fluid, comprising:
   a container means for holding said fluid;
   a balance arm having a first end attached to said container means, said arm having an inverted channel shaped crosssection which inverted channel shaped cross-section is terminated short of a second end of said balance arm, said balance arm including a calibration well disposed in a top surface of said balance arm between said termination of said inverted channel shaped cross-section and said second end of said balance arm, and said calibration well including a cylindrical shaped opening;
   a fulcrum means for supporting said balance arm;
   a balance weight slidably disposed on said balance arm; and
   cover means for covering said calibration well, said cover means including an upward extending part extending above a top surface of said balance arm to prevent said balance weight from sliding off said second end of said balance arm.

3. An apparatus for measuring density of a fluid, comprising:
   a container means for holding said fluid;
   a balance arm having a first end attached to said container means, said arm having an inverted channel shaped crosssection defined by a top portion and first and second side portions depending downwardly from said top portion, said balance arm including:
      a rib member extending downwardly from said top portion between said first and second side portions, said rib member having a first end connected to said container means and a second end which terminates between said first end of said balance arm and a second end of said balance arm;
      a first reinforcing web spanning between said top portion and said first and second side portions, said web being connected to said second end of said rib member and being located approximately one-third of the length of said balance arm away from said first end of said balance arm; and
      a second reinforcing web located approximately half way between said first reinforcing web and said second end of said second balance arm; and
   wherein said balance arm and said container means comprise a single integrally molded thermoplastic part, thereby providing a relatively lightweight and corrosion resistant density measuring apparatus.

* * * * *